(12) United States Patent
Lashinski

(10) Patent No.: US 8,372,108 B2
(45) Date of Patent: Feb. 12, 2013

(54) INTRAVASCULAR BLOOD FILTER

(75) Inventor: Randall T. Lashinski, Windsor, CA (US)

(73) Assignee: Claret Medical, Inc., Santa Rosa, CA (US)

( * ) Notice: Subject to any disclaimer, the term of this patent is extended or adjusted under 35 U.S.C. 154(b) by 412 days.

(21) Appl. No.: 12/689,997

(22) Filed: Jan. 19, 2010

(65) Prior Publication Data

US 2010/0185231 A1    Jul. 22, 2010

Related U.S. Application Data

(60) Provisional application No. 61/145,149, filed on Jan. 16, 2009.

(51) Int. Cl.
*A61M 29/00* (2006.01)

(52) U.S. Cl. .................................................. 606/200

(58) Field of Classification Search .................. None
See application file for complete search history.

(56) References Cited

U.S. PATENT DOCUMENTS

| | | | |
|---|---|---|---|
| 3,472,230 A | 10/1969 | Fogarty | |
| 4,619,246 A | 10/1986 | Molgaard-Nielsen et al. | |
| 4,650,466 A | 3/1987 | Luther | |
| 4,706,671 A | 11/1987 | Weinrib | |
| 4,723,549 A | 2/1988 | Wholey et al. | |
| 4,873,978 A | 10/1989 | Ginsburg | |
| 5,108,419 A | 4/1992 | Reger | |
| 5,192,286 A | 3/1993 | Phan | |
| 5,613,980 A | 3/1997 | Chauhan | |
| 5,662,671 A | 9/1997 | Barbut et al. | |
| 5,707,389 A | 1/1998 | Louw et al. | |
| 5,766,151 A | 6/1998 | Valley et al. | |
| 5,779,716 A | 7/1998 | Cano et al. | |
| 5,814,064 A | 9/1998 | Daniel | |
| 5,827,324 A | 10/1998 | Cassell | |
| 5,848,964 A | 12/1998 | Samuels | |
| 5,910,154 A | 6/1999 | Tsugita et al. | |
| 5,911,734 A | 6/1999 | Tsugita et al. | |
| 5,935,139 A | 8/1999 | Bates | |
| 5,980,555 A | 11/1999 | Barbut et al. | |
| 5,993,469 A | 11/1999 | McKenzie et al. | |
| 6,001,118 A | 12/1999 | Daniel | |
| 6,027,520 A | 2/2000 | Tsugita et al. | |
| 6,042,598 A | 3/2000 | Tsugita et al. | |
| 6,083,239 A | 7/2000 | Addis | |

(Continued)

FOREIGN PATENT DOCUMENTS

DE    10049812 A1    4/2002
EP    1253781 B1    12/2001

(Continued)

OTHER PUBLICATIONS

Lashinski, Randall; U.S. Appl. No. 12/844,420 entitled "Dual Endovascular Filter and Methods of Use," filed Jul. 27, 2010.

(Continued)

*Primary Examiner* — Gary Jackson
*Assistant Examiner* — Eric Blatt
(74) *Attorney, Agent, or Firm* — Knobbe, Martens, Olson & Bear, LLP.

(57) ABSTRACT

Disclosed is a novel filter and delivery means. The device described within will not interfere with standard practice and tools used during standard surgical procedures and tools such as cannulas, clamps or dissection instruments including valve replacement sizing gages or other surgical procedures where the patient must be put on a heart-lung machine cross-clamping the aorta.

7 Claims, 18 Drawing Sheets

U.S. PATENT DOCUMENTS

| | | | |
|---|---|---|---|
| 6,096,053 A | 8/2000 | Bates | |
| 6,142,987 A | 11/2000 | Tsugita | |
| 6,152,946 A | 11/2000 | Broome et al. | |
| 6,171,328 B1 | 1/2001 | Addis | |
| 6,179,851 B1 | 1/2001 | Barbut et al. | |
| 6,235,045 B1 | 5/2001 | Barbut et al. | |
| 6,245,088 B1 | 6/2001 | Lowery | |
| 6,245,089 B1 | 6/2001 | Daniel | |
| 6,264,663 B1 | 7/2001 | Cano | |
| 6,270,513 B1 | 8/2001 | Tsugita et al. | |
| 6,325,815 B1 | 12/2001 | Kusleika et al. | |
| 6,336,934 B1 | 1/2002 | Gilson et al. | |
| 6,346,116 B1 | 2/2002 | Brooks et al. | |
| 6,361,545 B1 | 3/2002 | Macoviak et al. | |
| 6,371,971 B1 | 4/2002 | Tsugita et al. | |
| 6,485,502 B2 | 11/2002 | Don Michael et al. | |
| 6,558,356 B2 | 5/2003 | Barbut | |
| 6,605,102 B1 | 8/2003 | Mazzocchi et al. | |
| 6,620,148 B1 | 9/2003 | Tsugita | |
| 6,663,652 B2 | 12/2003 | Daniel et al. | |
| 6,676,682 B1 | 1/2004 | Tsugita et al. | |
| 6,712,835 B2 | 3/2004 | Mazzocchi | |
| 6,726,701 B2 | 4/2004 | Gilson et al. | |
| 6,740,061 B1 | 5/2004 | Oslund et al. | |
| 6,843,798 B2 | 1/2005 | Kusleika et al. | |
| 6,872,216 B2 | 3/2005 | Daniel | |
| 6,887,258 B2 | 5/2005 | Denison et al. | |
| 6,905,490 B2 | 6/2005 | Parodi | |
| 7,048,752 B2 | 5/2006 | Mazzocchi | |
| 7,094,249 B1 | 8/2006 | Broome et al. | |
| 7,115,134 B2 * | 10/2006 | Chambers | 606/108 |
| 7,160,255 B2 | 1/2007 | Saadat | |
| 7,169,165 B2 | 1/2007 | Belef et al. | |
| 7,214,237 B2 | 5/2007 | Don Michael et al. | |
| 7,323,001 B2 | 1/2008 | Clubb et al. | |
| 7,410,491 B2 | 8/2008 | Hopkins | |
| 7,493,154 B2 | 2/2009 | Bonner et al. | |
| 7,559,925 B2 | 7/2009 | Goldfarb et al. | |
| 7,922,732 B2 | 4/2011 | Mazzocchi et al. | |
| 2002/0055767 A1 | 5/2002 | Forde et al. | |
| 2002/0077596 A1 | 6/2002 | McKenzie et al. | |
| 2002/0095172 A1 | 7/2002 | Mazzocchi et al. | |
| 2002/0123761 A1 | 9/2002 | Barbut et al. | |
| 2003/0100919 A1 | 5/2003 | Hopkins et al. | |
| 2003/0171770 A1 | 9/2003 | Kusleika et al. | |
| 2004/0002730 A1 | 1/2004 | Denison et al. | |
| 2004/0215167 A1 | 10/2004 | Belson | |
| 2004/0220611 A1 | 11/2004 | Ogle | |
| 2004/0243175 A1 | 12/2004 | Don Michael | |
| 2004/0254601 A1 | 12/2004 | Eskuri | |
| 2004/0254602 A1 | 12/2004 | Lehe et al. | |
| 2005/0080356 A1 | 4/2005 | Dapolito et al. | |
| 2005/0101987 A1 | 5/2005 | Salahieh | |
| 2005/0137696 A1 | 6/2005 | Salahieh | |
| 2006/0015136 A1 | 1/2006 | Besselink | |
| 2006/0030877 A1 | 2/2006 | Martinez et al. | |
| 2006/0100658 A1 | 5/2006 | Obana et al. | |
| 2006/0129180 A1 | 6/2006 | Tsugita et al. | |
| 2006/0161241 A1 | 7/2006 | Barbut et al. | |
| 2006/0259066 A1 | 11/2006 | Euteneuer | |
| 2008/0004687 A1 | 1/2008 | Barbut et al. | |
| 2008/0058860 A1 | 3/2008 | Demond et al. | |
| 2008/0065145 A1 | 3/2008 | Carpenter | |
| 2008/0065147 A1 | 3/2008 | Mazzocchi et al. | |
| 2008/0125848 A1 | 5/2008 | Kusleika et al. | |
| 2008/0188884 A1 | 8/2008 | Gilson et al. | |
| 2008/0234722 A1 | 9/2008 | Bonnette et al. | |
| 2008/0262442 A1 | 10/2008 | Carlin et al. | |
| 2009/0024153 A1 | 1/2009 | Don Michael | |
| 2009/0069840 A1 | 3/2009 | Hallisey | |
| 2009/0198269 A1 | 8/2009 | Hannes et al. | |
| 2009/0203962 A1 | 8/2009 | Miller et al. | |
| 2009/0254172 A1 | 10/2009 | Grewe et al. | |
| 2009/0326575 A1 * | 12/2009 | Galdonik et al. | 606/200 |
| 2010/0004633 A1 | 1/2010 | Rothe et al. | |
| 2010/0063537 A1 | 3/2010 | Ren et al. | |
| 2010/0179583 A1 | 7/2010 | Carpenter et al. | |
| 2010/0179584 A1 | 7/2010 | Carpenter et al. | |
| 2010/0179585 A1 | 7/2010 | Carpenter et al. | |
| 2010/0179647 A1 | 7/2010 | Carpenter et al. | |
| 2010/0185231 A1 | 7/2010 | Lashinski | |
| 2010/0211095 A1 | 8/2010 | Carpenter | |
| 2010/0312268 A1 | 12/2010 | Belson | |
| 2010/0324589 A1 | 12/2010 | Carpenter et al. | |
| 2011/0066221 A1 * | 3/2011 | White et al. | 623/1.11 |

FOREIGN PATENT DOCUMENTS

| | | |
|---|---|---|
| EP | 1400257 A2 | 3/2004 |
| WO | WO 99/23976 A1 | 5/1999 |
| WO | WO 2004/026175 | 4/2004 |
| WO | WO 2008/100790 A2 | 8/2008 |
| WO | WO 2008/113857 | 9/2008 |
| WO | WO 2010/083527 A2 | 7/2010 |
| WO | WO 2010/088520 A2 | 8/2010 |
| WO | WO 2011/034718 A2 | 3/2011 |
| WO | WO 2011/017103 A2 | 10/2011 |
| WO | PCT/US2011/067598 | 12/2011 |

OTHER PUBLICATIONS

Lee et al.; U.S. Appl. No. 12/871,708 entitled "Intravascular Blood Filters and Methods of Use," filed Aug. 30, 2010.

Lashinski, Randall; U.S. Appl. No. 12/696,926 entitled "Illuminated Intravascular Blood Filter," filed Jan. 29, 2010.

International Search Report in Application No. PCT/US2010/021417 dated Aug. 23, 2010, in 4 pages.

International Search Report in Application No. PCT/US2010/047166 dated Apr. 27, 2011, in 7 pages.

International Search Report in Application No. PCT/US2010/043390 dated Apr. 8, 2011, in 11 pages.

International Search Report in Application No. PCT/US2011/067598 dated May 10, 2012, in 7 pages.

International Preliminary of Patentability in Application No. PCT/US2010/022590 dated Jan. 29, 2010, in 4 pages.

Supplementary European Search Report in Application No. PCT/US2010/021417 dated Nov. 28, 2012, in 5 pages.

\* cited by examiner

INTRAVASCULAR BLOOD FILTER

CROSS-REFERENCE TO RELATED APPLICATIONS

This application claims the benefit of U.S. Provisional Application No. 61/145,149, filed Jan. 16, 2009, entitled "Intravascular Blood Filter," the disclosure of which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

This invention relates generally to medical devices used during vascular intervention, and more particularly, concerns medical devices that are useful in treating aortic valve replacement, thromboembolic disorders and for removal of foreign bodies in the vascular system.

Thromboembolic disorders, such as stroke, pulmonary embolism, peripheral thrombosis, atherosclerosis, and the like, affect many people. These disorders are a major cause of morbidity and mortality in the United States and throughout the world. Thromboembolic events are characterized by an occlusion of a blood vessel. The occlusion can be caused by a clot which is viscoelastic (jelly-like) and is comprised of platelets, fibrinogen, and other clotting proteins.

Percutaneous aortic valve replacement has been in development for some time now and stroke rates related to this procedure are between four and twenty percent. During catheter delivery and implantation plaque may be dislodged from the vasculature. The invention contained within will block the emboli from traveling through the carotid circulation and onto the brain. When an artery is occluded by a clot, tissue ischemia (lack of oxygen and nutrients) develops. The ischemia will progress to tissue infarction (cell death) if the occlusion persists. Infarction does not develop or is greatly limited if the flow of blood is reestablished rapidly. Failure to reestablish blood-flow can lead to the loss of limb, angina pectoris, myocardial infarction, stroke, or even death.

Occlusion of the venous circulation by thrombi leads to blood stasis which can cause numerous problems. The majority of pulmonary embolisms are caused by emboli that originate in the peripheral venous system. Reestablishing blood flow and removal of the thrombus is highly desirable.

There are many existing techniques employed to reestablish blood flow in an occluded vessel. One common surgical technique, an embolectomy, involves incising a blood vessel and introducing a balloon-tipped device (such as a Fogarty catheter) to the location of the occlusion. The balloon is then inflated at a point beyond the clot and used to translate the obstructing material back to the point of incision. The obstructing material is then removed by the surgeon. While such surgical techniques have been useful, exposing a patient to surgery may be traumatic and is best avoided when possible. Additionally, the use of a Fogarty catheter may be problematic due to the possible risk of damaging the interior lining of the vessel as the catheter is being withdrawn.

A common percutaneous technique is referred to as balloon angioplasty where a balloon-tipped catheter is introduced into a blood vessel, typically through an introducing catheter. The balloon-tipped catheter is then advanced to the point of the occlusion and inflated in order to dilate the stenosis. Balloon angioplasty is appropriate for treating vessel stenosis but is generally not effective for treating acute thromboembolisms.

Another percutaneous technique is to place a microcatheter near the clot and infuse Streptokinase, Urokinase, or other thrombolytic agents to dissolve the clot. Unfortunately, thrombolysis typically takes hours to days to be successful. Additionally, thrombolytic agents can cause hemorrhage and in many patients the agents cannot be used at all.

Another problematic area is the removal of foreign bodies. Foreign bodies introduced into the circulation can be fragments of catheters, pace-maker electrodes, guide wires, and erroneously placed embolic material such as thrombogenic coils. There exist retrieval devices for the removal of foreign bodies, certain of such devices form a loop that can ensnare the foreign material by decreasing the size of the diameter of the loop around the foreign body. The use of such removal devices can be difficult and sometimes unsuccessful.

Moreover, systems heretofore disclosed in the art are generally limited by size compatibility and the increase in vessel size as the emboli is drawn out from the distal vascular occlusion location to a more proximal location near the heart. If the embolectomy device is too large for the vessel it will not deploy correctly to capture the clot or foreign body, and if too small in diameter it cannot capture clots or foreign bodies across the entire cross section of the blood vessel. Additionally, if the embolectomy device is too small in retaining volume then as the device is retracted the excess material being removed can spill out and be carried by flow back to occlude another distal vessel.

Various thrombectomy and foreign matter removal devices have been disclosed in the art. However, such devices have been found to have structures which are either highly complex or lacking in sufficient retaining structure. Disadvantages associated with the devices having highly complex structure include difficulty in manufacturability as well as difficulty in use in conjunction with microcatheters. Recent developments in the removal device art features umbrella filter devices having self folding capabilities. Typically, these filters fold into a pleated condition, wherein the pleats extend radially and can obstruct retraction of the device into the microcatheter sheathing.

What has been needed and heretofore unavailable is an extraction device that can be easily and controllably deployed into and retracted from the circulatory system for the effective removal of clots and foreign bodies. There is also a need for a system that can be used as a temporary arterial or venous filter to capture and remove thromboemboli generated during endovascular procedures. Moreover, due to difficult-to-access anatomy such as the cerebral vasculature and the neurovasculature, the invention should possess a small collapsed profile and preferably be expandable to allow the device to be delivered through the lumen of commercially available catheters. The present invention satisfies these needs.

SUMMARY OF THE INVENTION

Most filter devices are delivered from the groin and are placed distal to the flow of the lesion or site in question. Single basket-type filters or Nitinol loop filters are the most common used today in carotid stent procedures of vein graft stenting. As the guidewire is delivered past the lesion the filter is delivered over the guidewire protecting the distal vasculature. The invention here may be delivered from the groin in a conventional manner to vessels such as the carotid arteries or via radial (arm vasculature) approach. Protecting the carotid arteries and cerebral vasculature system is the main goal while leaving the aortic arch free from catheters and wire as much as possible during the delivery of other devices such as aortic balloons and prosthetic valves or other associated devices.

One method of filtering the carotid arteries leaving the aorta free from obstruction is to deliver a filter to each of the carotid arteries from the groin leaving them in the carotid vasculature and retrieving them via snare post procedure. A delivery catheter would be inserted through an introducer in the groin (femoral artery) and delivered to the common carotid arteries and detached. The delivery catheter would be removed and a second filter would be delivered in a similar manner to the other carotid artery. With two detached filters now in place the procedure treating the aortic or mitral valve can now be completed with embolic protection for the cerebral vascular system. Once the procedure to the valve is completed, the filters can be snared and retrieved back out the femoral artery as they were delivered. Any embolic particles will be captured in the filter device and removed safely from the body.

Another method for filtering the carotid arteries would be to deliver a filter from the femoral artery and utilize a single catheter to house the two attachment means to the filters. These attachments may be a wire similar to a guidewire or a hypo-tube to connect the filter element to an external portion of the body. Keeping these wires or connection means organized and contained within a single or dual lumen catheter will help organize and limit potential entanglement with other catheters being delivered to the target site such as the aortic valve or other cardiac elements including but not limited to the mitral valve and coronary arteries. The distal portion of the catheter may have a single exit portion or a staggered exit to allow an exit at different points along the catheter. One exit port may be at the distal most end of the catheter and the other may be a centimeter proximal from this to allow the attachment wire to exit near the left common carotid artery. Furthermore, there could be an extension to the distal most portion of the catheter allowing side ports for both wires to exit. This would allow for additional catheter stabilization within the aorta.

Another embodiment would deliver filters to the carotid from the radial artery and allow for a clear aortic arch from catheters and other delivery means from a more conventional femoral delivery means. From this access site a plurality of filters could be delivered through a common access sheath or the filters could be delivered from a dual lumen catheter with each lumen housing a single filter.

Another delivery means would utilize a single catheter with filters mounted in a coaxial manner where the distal filter would be delivered first and could be mounted to a wire where the second would be mounted to a hypo-tube where the first filters wire would run through the second allowing for relative motion between the two filters. The first filter would be delivered to the left common carotid from the radial artery and the second would be delivered to the right common carotid artery or the brachiocephalic trunk in a coaxial manner. These filters would be opposed in direction as the distal filter would be filtering blood flowing from the base of the aorta to the head and toward the distal end of the guidewire. The proximal filter would be filtering blood from the base of the aorta to the head and toward the proximal end of the guidewire. Placing the two filters together there would be a conical shape configuration where the large diameter portions of the cones would meet. These two filters would be delivered in a collapsed configuration and expanded when expelled from the delivery catheter. Retrieval would be a retraction of the filter back into a recovery catheter that would be a larger inner diameter than the delivery catheter to allow room for particulate. Being opposed in capture direction the right carotid would be the first filter that would be recovered by an expanded sheath where the embolic material would not be disturbed and further withdrawn to a smaller sheath for removal from the body. The expanded sheath could be constructed from braided Nitinol wire pre-shaped so when exposed the braid would expand to receive the filter without squeezing out any trapped emboli. The second or left carotid filter would be recovered in a conventional manner where the larger diameter would be pulled into a sheath to trap and remove the emboli within the tail or distal portion of the filter.

Another means to deliver the filters via radial artery approach would be to utilize a dual lumen catheter where each lumen would house a single filter. The first lumen would deliver a filter to the left carotid artery and the second lumen would deliver a filter to the right carotid artery. The lumens could be staggered in length to reach each ostium in which case the first or left filter lumen would be longer in length to allow for placement distal from the second filter placement in the right carotid. Additionally, the second lumen may be pre-shaped with a curve to allow easy access to the right carotid artery. This pre-shaped curve may be retained in a straighter manner to allow for delivery and released to express the delivery shape when at the bifurcation of the subclavian and the carotid artery. Furthermore, there may be an active shaping where the curve is directed external to the body by a handle mechanism such as a pull-wire where tension would generate a compressive force to the catheter column preferentially bending the lumen. Recovery could utilize the same dual lumen concept or utilize a second recovery sheath independently from one another.

Another application for this device and method would be for surgical operations where the patient may be put on heart-lung bypass. During cross clamping of the aorta catheters or wires in the aorta may interfere with the procedure and allow leakage of blood around the cannulas used. If any of the above described devices or techniques are used before the patient's chest is opened this filtration of the carotid vessels would protect from emboli thus reducing the stroke risk during and after the procedure. Additional antithrombotic coatings to the filter could allow for an extended implantation time allowing filtration time to be extended post procedure. An example of this coating would be Heparin. Placement of these catheters and filters could be under fluoroscopy or ultrasound guidance to direct proper filter placement. Radiopaque markers may add necessary visibility to the catheter, filter and or wires.

Another surgical delivery means would be an insertion to the carotid artery via the neck. The filter could face either antigrade or retrograde depending upon the placement insertion point or access site. This would allow for complete filtration without any aortic interference as the entire devices would be within the carotid circulation. With this delivery technique the puncture site would be very small and recovery could be through the entry site or through the groin as the filter could be inserted distal to meet a recovery sheath in the aorta. With this groin recovery any emboli within the proximal carotid would be captured before later dislodgement.

Intravascular filters have been used in many configurations ranging from a windsock style as commercialized as the FilterWire from Boston Scientific or the ACCUNET from Abbott Vascular or the Spider from eV3. These filters utilize a memory metal such as Nitinol is used to oppose the vascular wall tightly sealing any emboli from passage while a filter material such as a porous fabric material retains and emboli from passing distally from the device. Another example is a laser cut memory metal where the basket is the frame and the filter is used to trap emboli when expanded. Another example is constructed from a braided wire such as Medtronic's Interceptor PLUS where once exposed the braid expands to create a funnel or cone shape to trap emboli and the proximal or larger end is pre-shaped to accept blood flow with larger openings heat-set into the memory metal such as Nitinol. These filters range in diameter from about 2-15 mm in diameter and are approximately 20-30 mm in length. They are generally attached to a guidewire and sheathed for delivery and resheathed for recovery. The catheter profile measures about 1 to 2 mm in diameter and has a length of about 90 to 200 cm. Catheter construction is normally a polypropylene or polyethylene material but nylons and blends can be used as well. All devices are considered single use and are commonly placed for carotid stenting or savenous veign grafts stenting.

DETAILED DESCRIPTION OF THE PREFERRED EMBODIMENT

Figure 1:
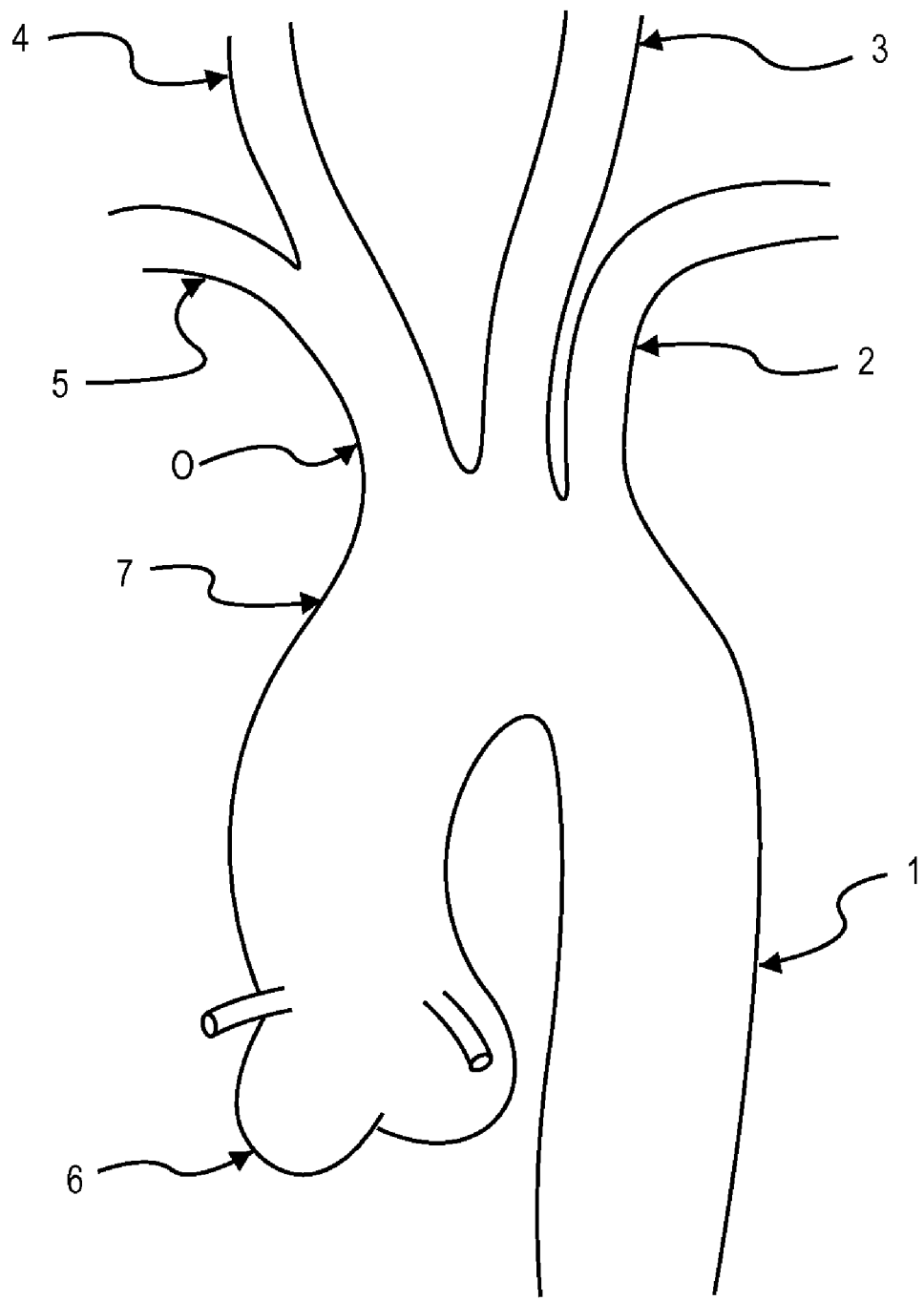
FIG. 1 illustrates the vascular anatomy of the aorta and surrounding great vessels.
Figure 2:
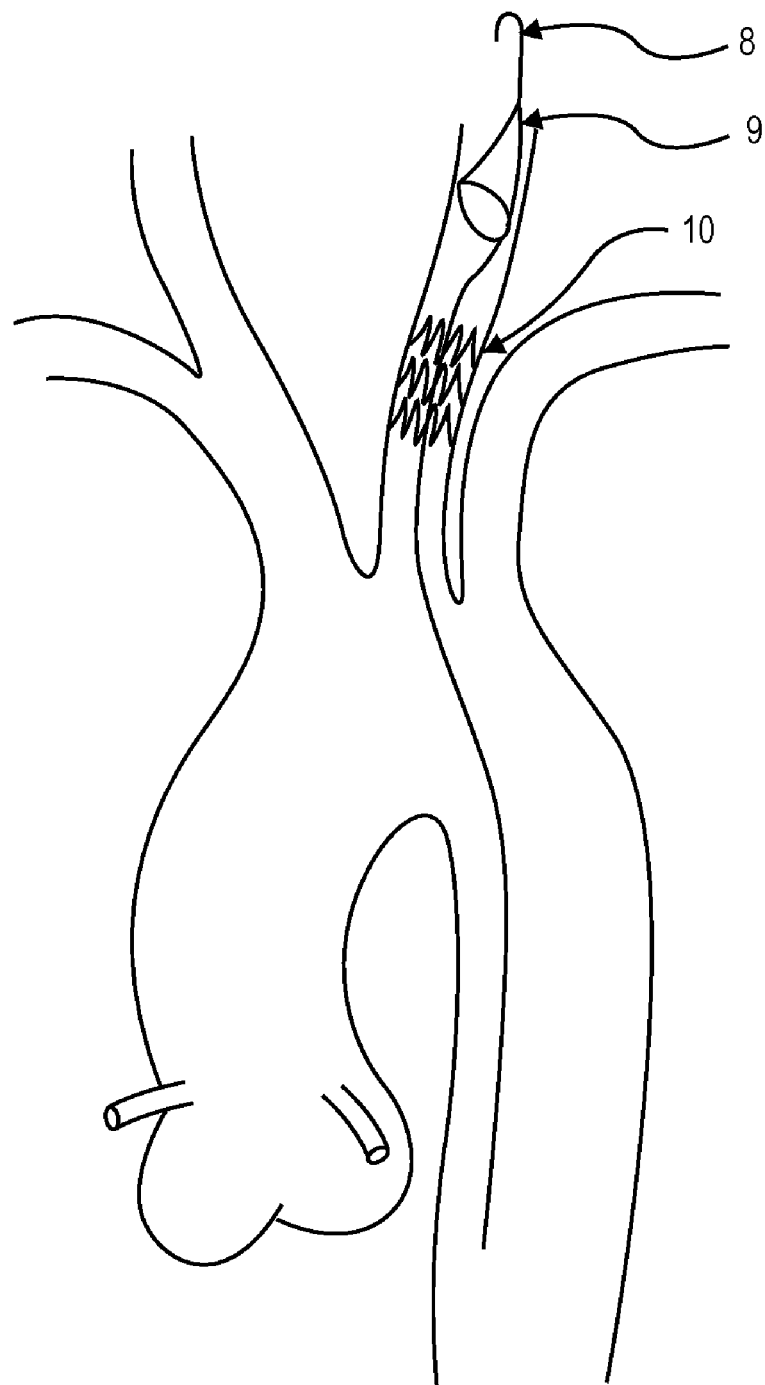
FIG. 2 illustrates the common technique in carotid filter 8 insertion for carotid stenting 10 as delivered via femoral artery over a guidewire 9.
Figure 3:
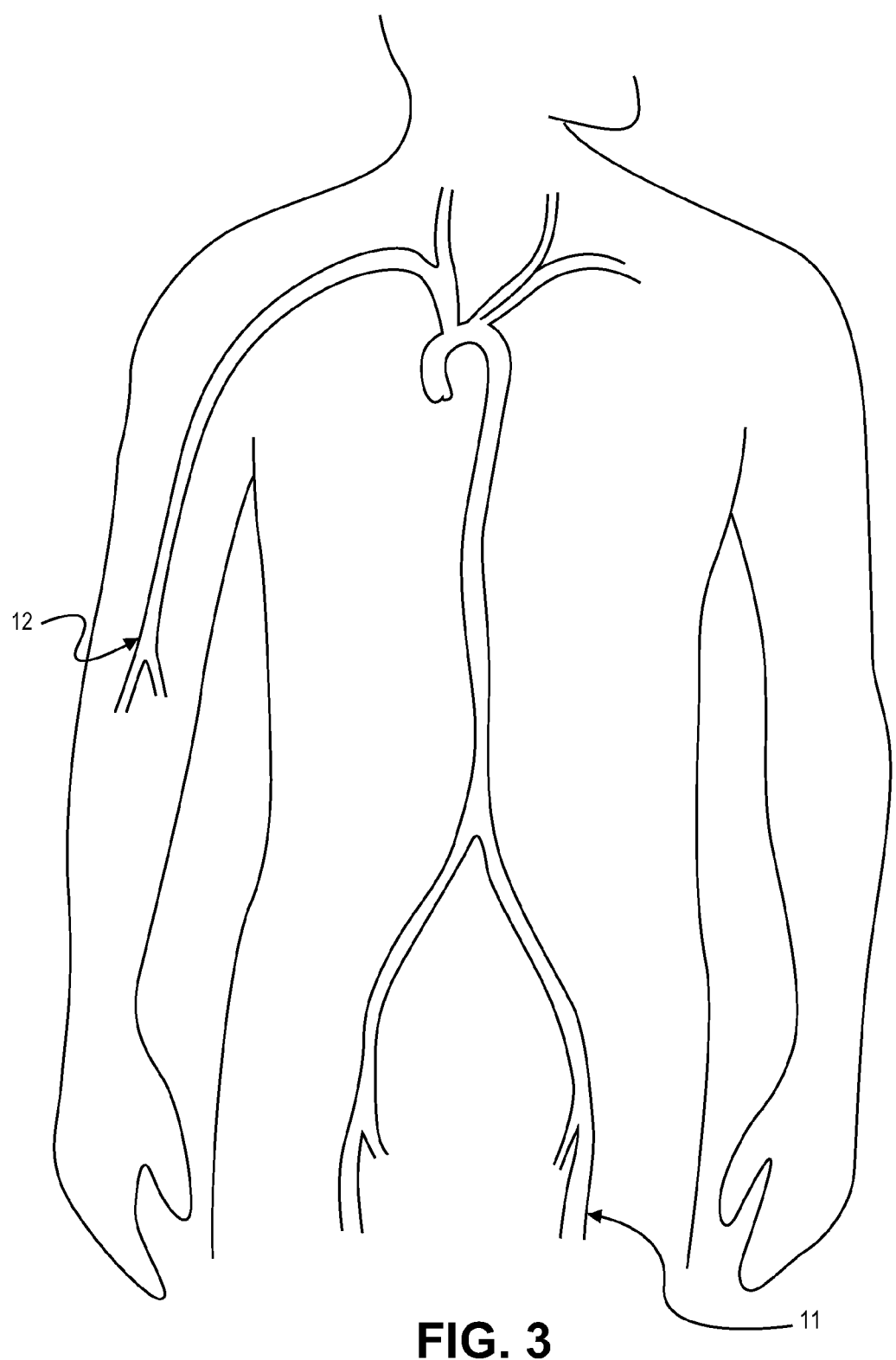
FIG. 3 illustrates the aortic vasculature where sheaths could be placed by the interventional cardiologist. The right femoral 11 being the most common access as the cardiologist works from the right side of the patient which is presented to the physician while on the table. The right radial artery 12 has been used but due to the small diameter of the vessel is not a common insertion point for the cardiologist.
Figure 4:
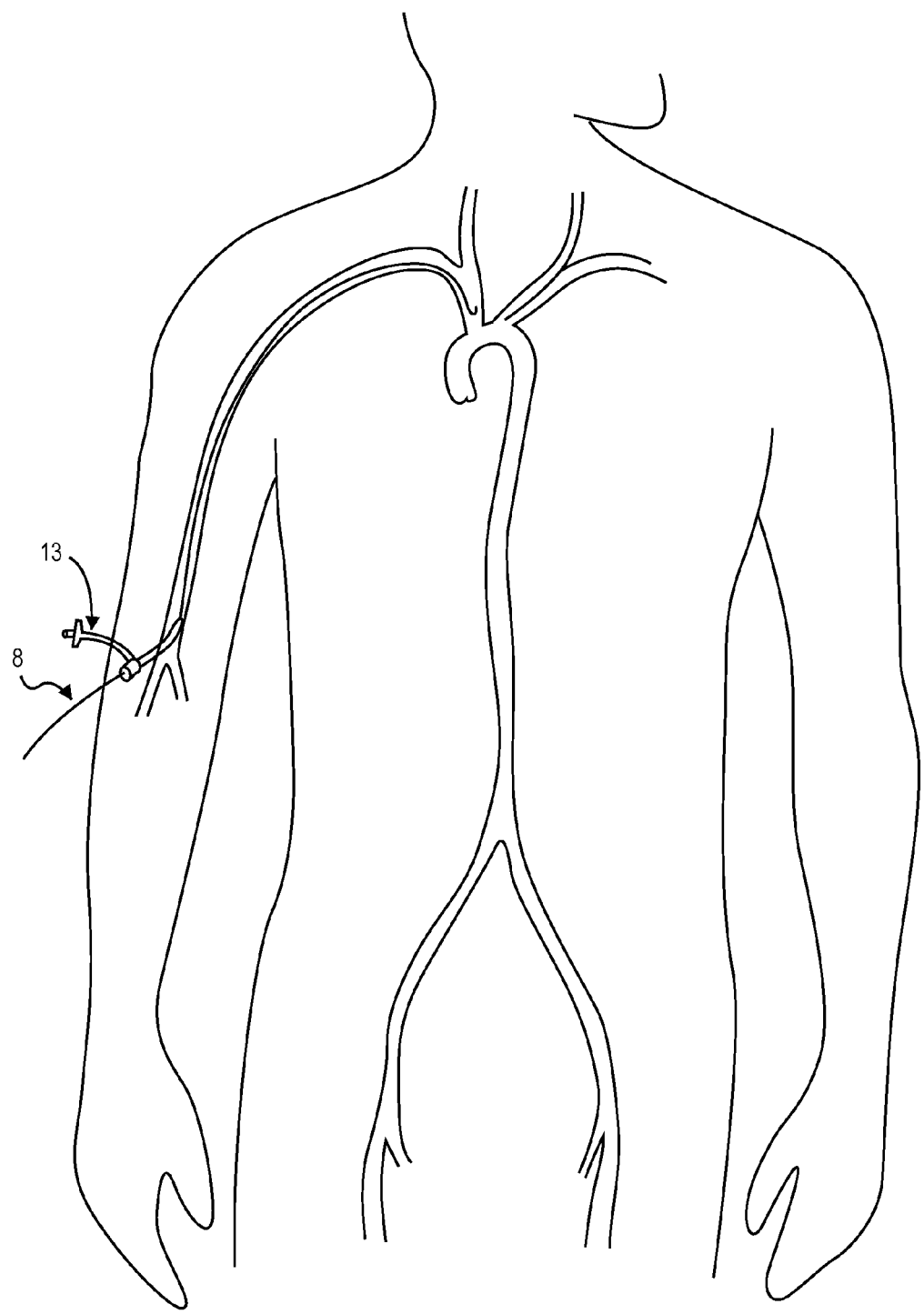
FIG. 4 illustrates a brachial entry with common introducer 13 and guidewire 8 techniques.
Figure 5:
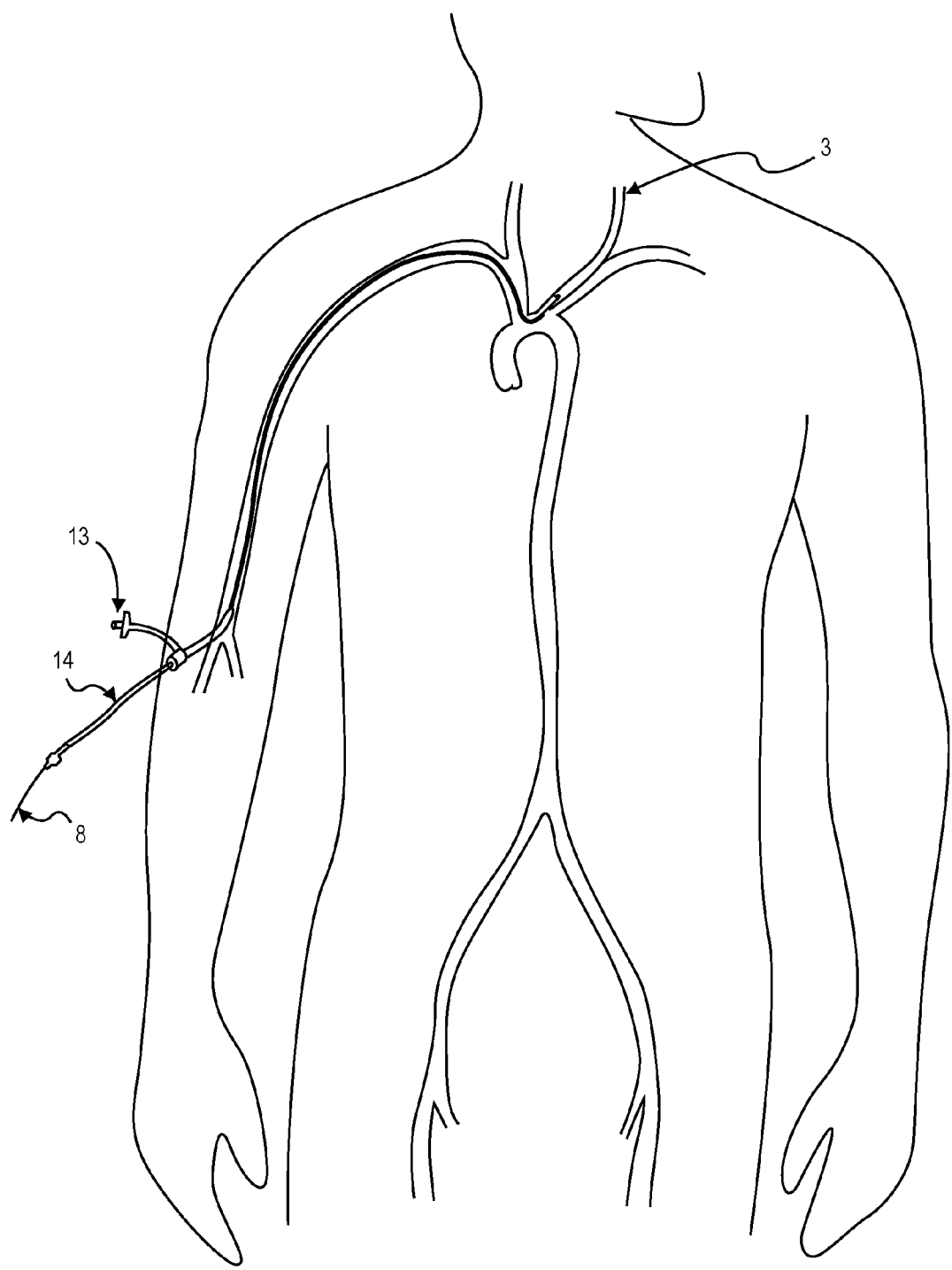
FIG. 5 illustrates the guide catheter 14 being inserted to the introducer 13 over the guidewire 8 in a brachial artery entry where the guide catheter 14 has a preshaped distal section to access the left common carotid 3.
Figure 6:
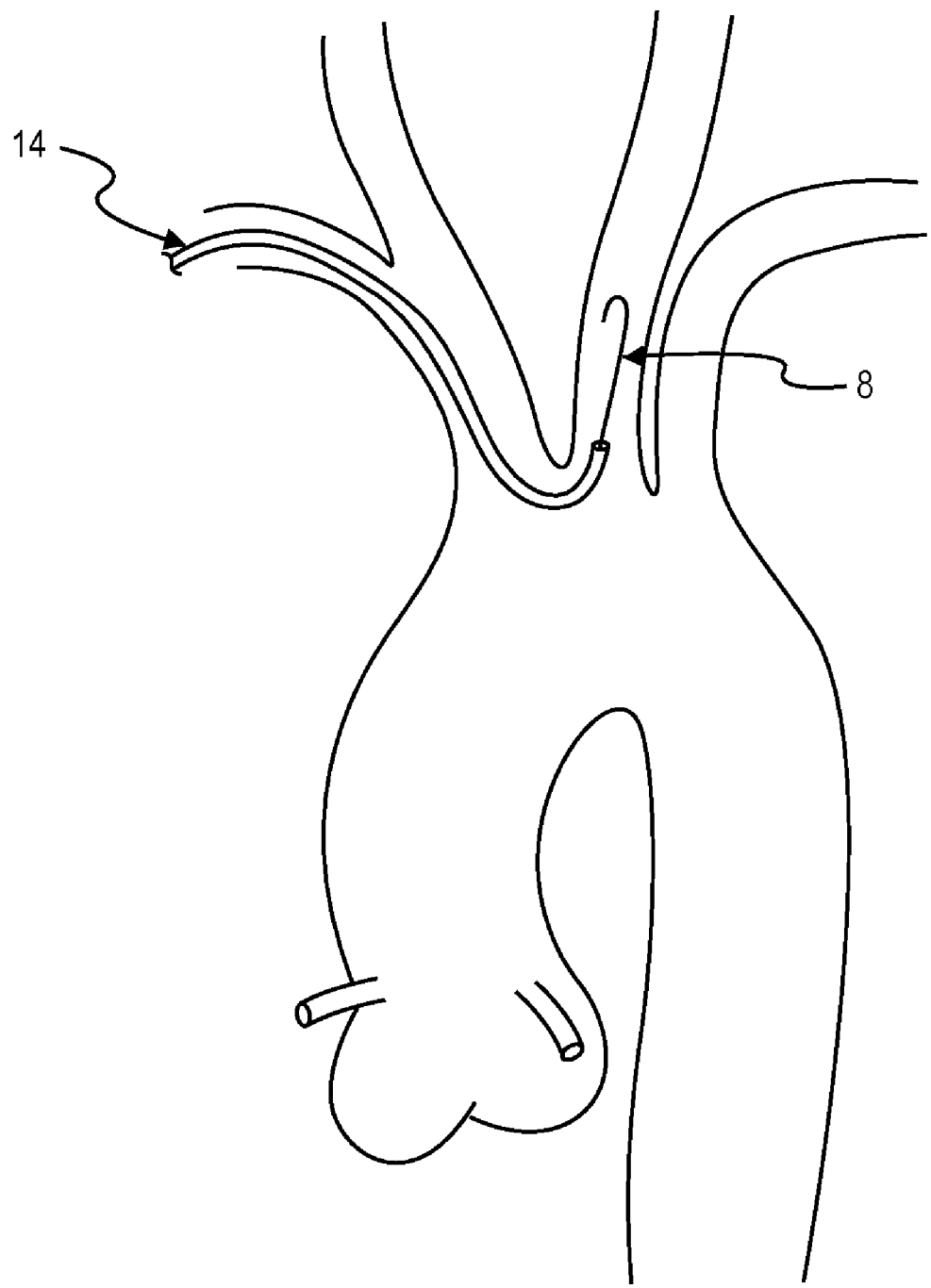
FIG. 6 illustrates a closer view of the guide catheter 14 and guidewire 8 accessing the left carotid artery where the first filter would be placed.
Figure 7:
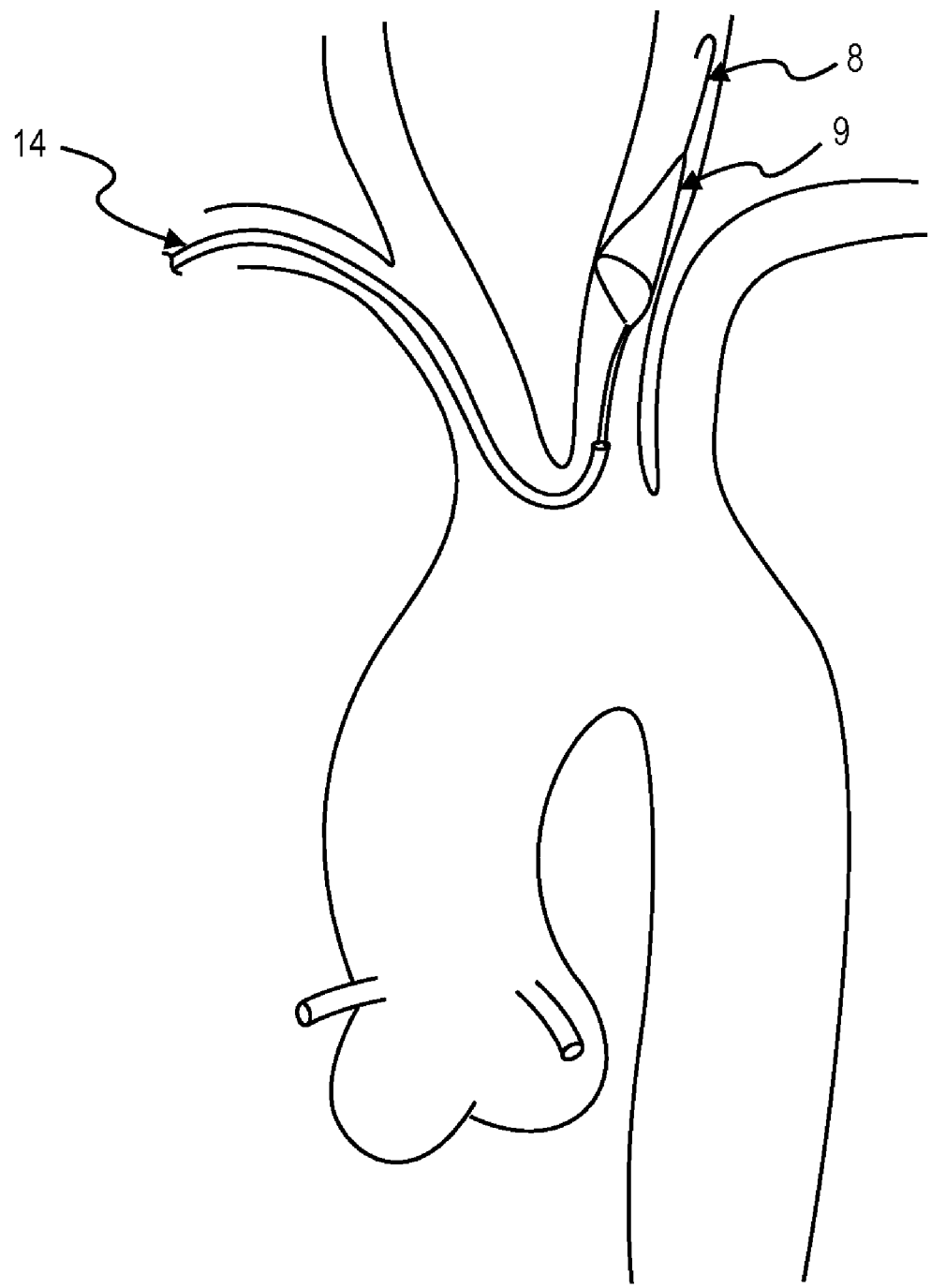
FIG. 7 illustrates the deployment of the first filter 9 through the guide catheter 14 over a guidewire 8 where the filter 9 is fully opposed to the left carotid artery.
Figure 8:
FIG. 8 illustrates both filters 9 deployed and protecting the carotid arteries utilizing a common guidewire 8 and common guide catheter 14.
Figure 9:
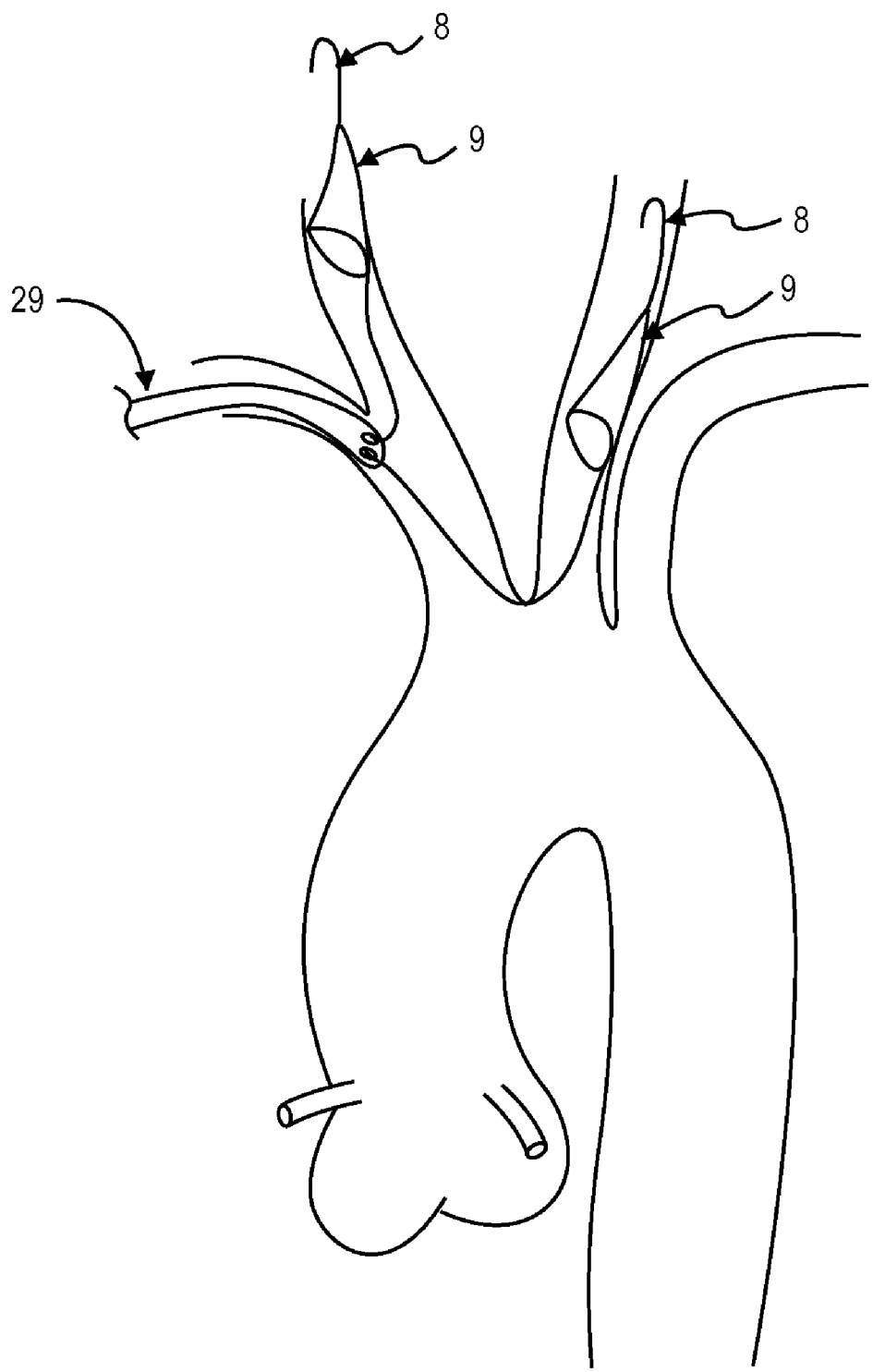
FIG. 9 illustrates a dual lumen catheter 29 where each filter 9 has a single guidewire 8. Both filters 9 are in a conventional orientation where the flow is in the distal direction or toward the distal tip of the guidewire 8. Independent recovery of the filters 9 could occur or a common recovery sheath may be used to load both into one sheath.
Figure 10:
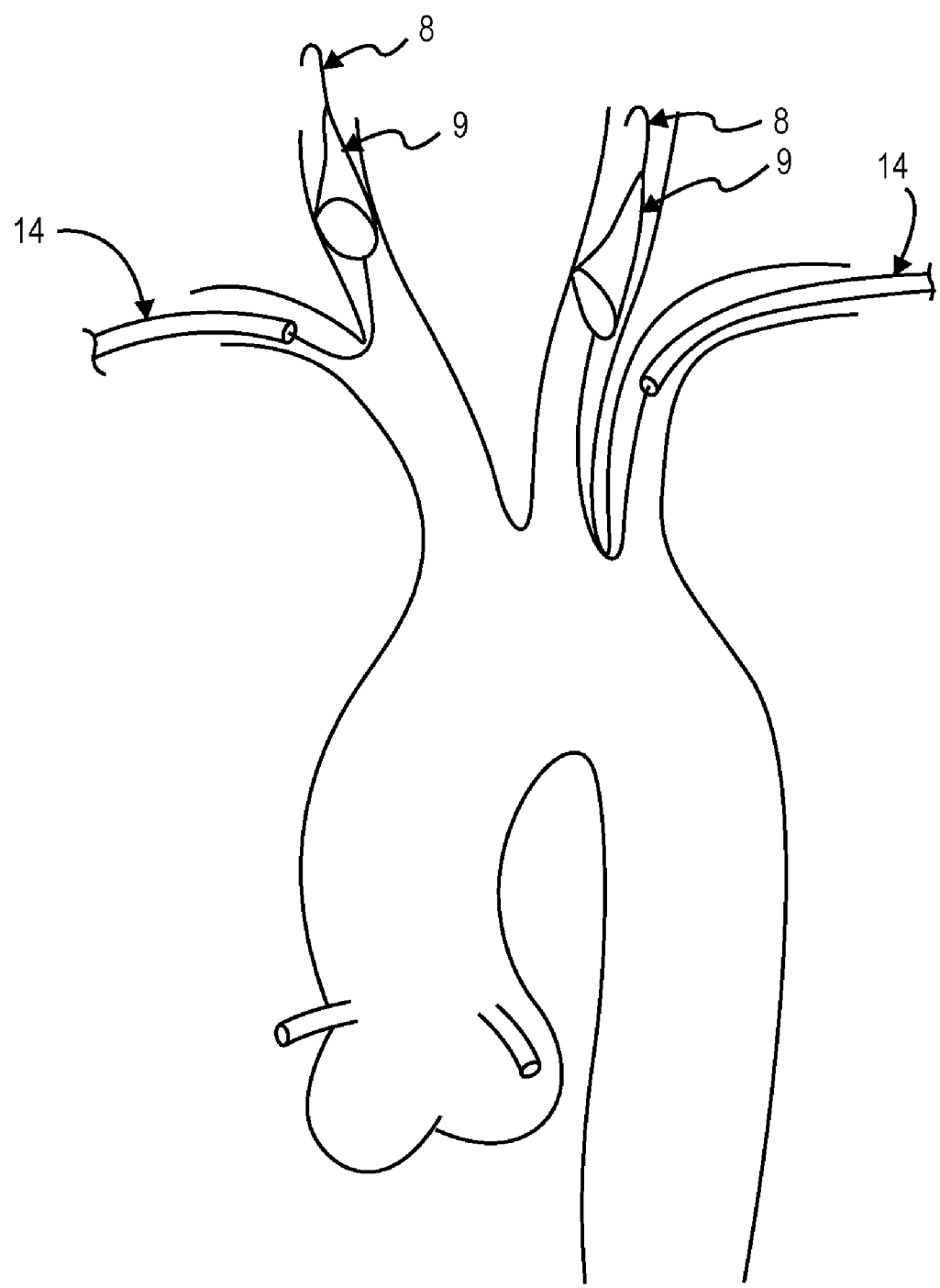
FIG. 10 illustrates both filters 9 being delivered via subclavian where the left filter is delivered via left subclavian artery with an entry point in the radial artery. Each delivery would include a guidewire 8 and a guide catheter 14 where a pre-shaped curve would allow access into the respective carotid artery.
Figure 11:
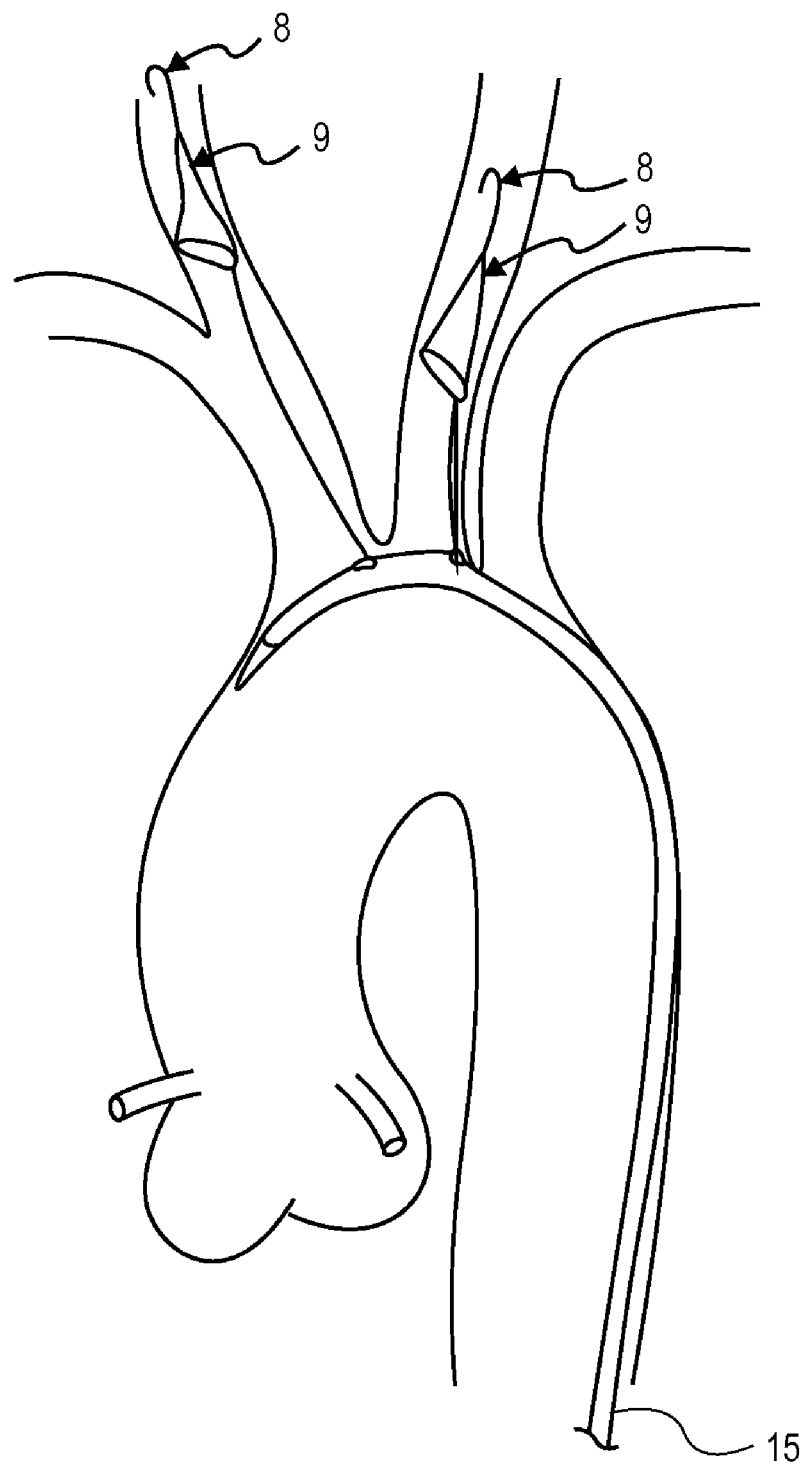
FIG. 11 illustrates a single organization catheter 15 to retain two filter 9 guidewires 8 controlling the potential for entanglement with each wire or other catheters introduced to the body. These catheters would include pigtail catheters used for contrast injections, balloon catheters for dilation or other catheters for delivery of therapeutic agents or implantable devices such as stents or prosthetic heart valves where the catheters are generally larger (18-26 French) in diameter. The catheter would have two distal exit ports to allow each filter to exit at the respective ostia. A distal section would extend beyond the brachiocephalic trunk allowing for a smooth shape to the catheter and ensure it is close to the outer radius of the arch.
Figure 12:
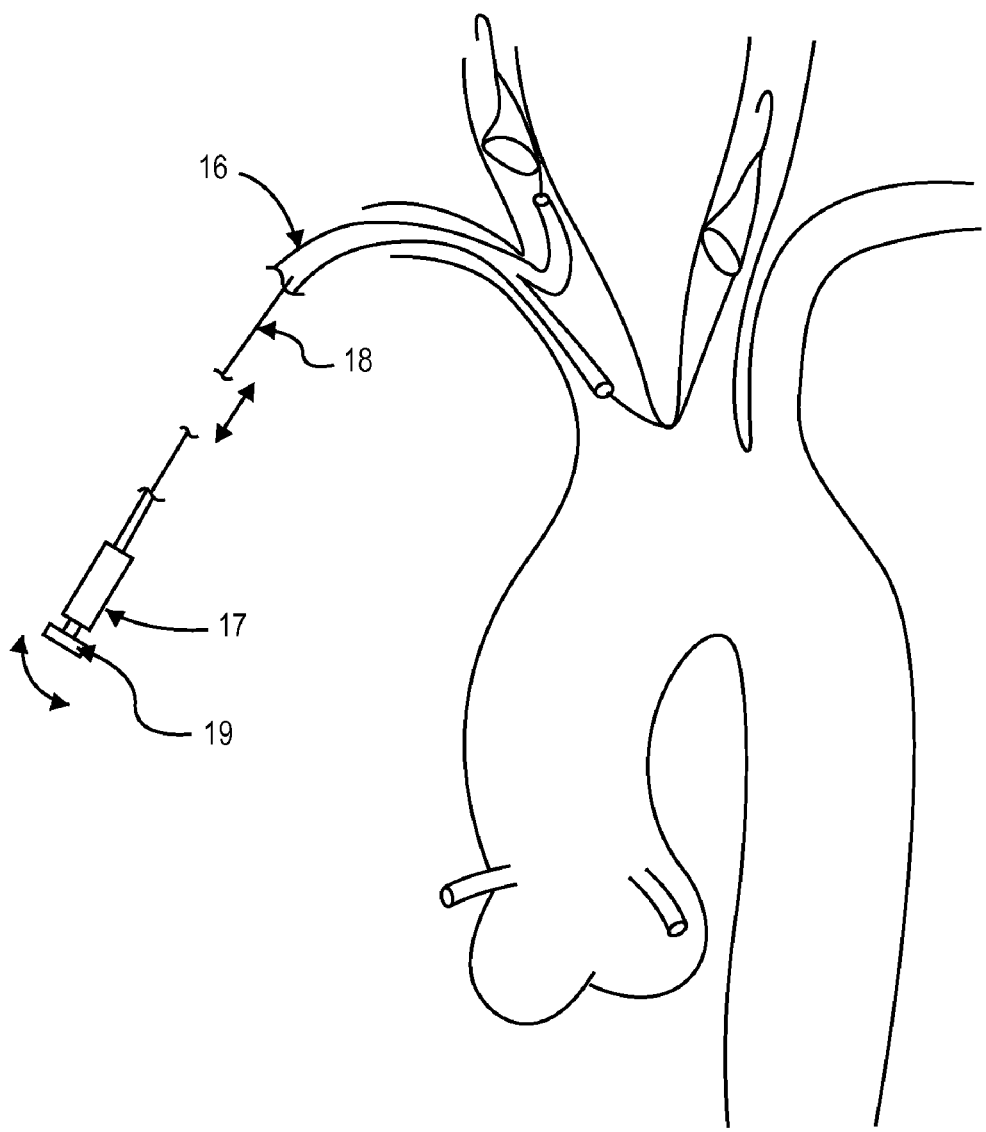
FIG. 12 illustrates a dual lumen catheter 16 with an active curving mechanism to steer each lumen to the respected carotid artery. The deflection will allow for active steering of each distal section to account for any differences in anatomy from patient to patient. Similar to electrophysiology catheters a deflection wire 18 could be tensioned to provide a bias or curve to tip. The delivery of each filter would be in a conventional orientation where the blood flow would be in the distal direction and toward the tip of the guidewire. External to the body would be a handle mechanism 17 providing an actuation force to the distal portion of the catheter. This actuation could be a rotational knob 19 translating a rotation movement to a screw mechanism providing a tension to a wire connected to the catheter tip. Other methods could include an electrical signal to drive a motion or hydraulic actuation to translate a force.
Figure 13:
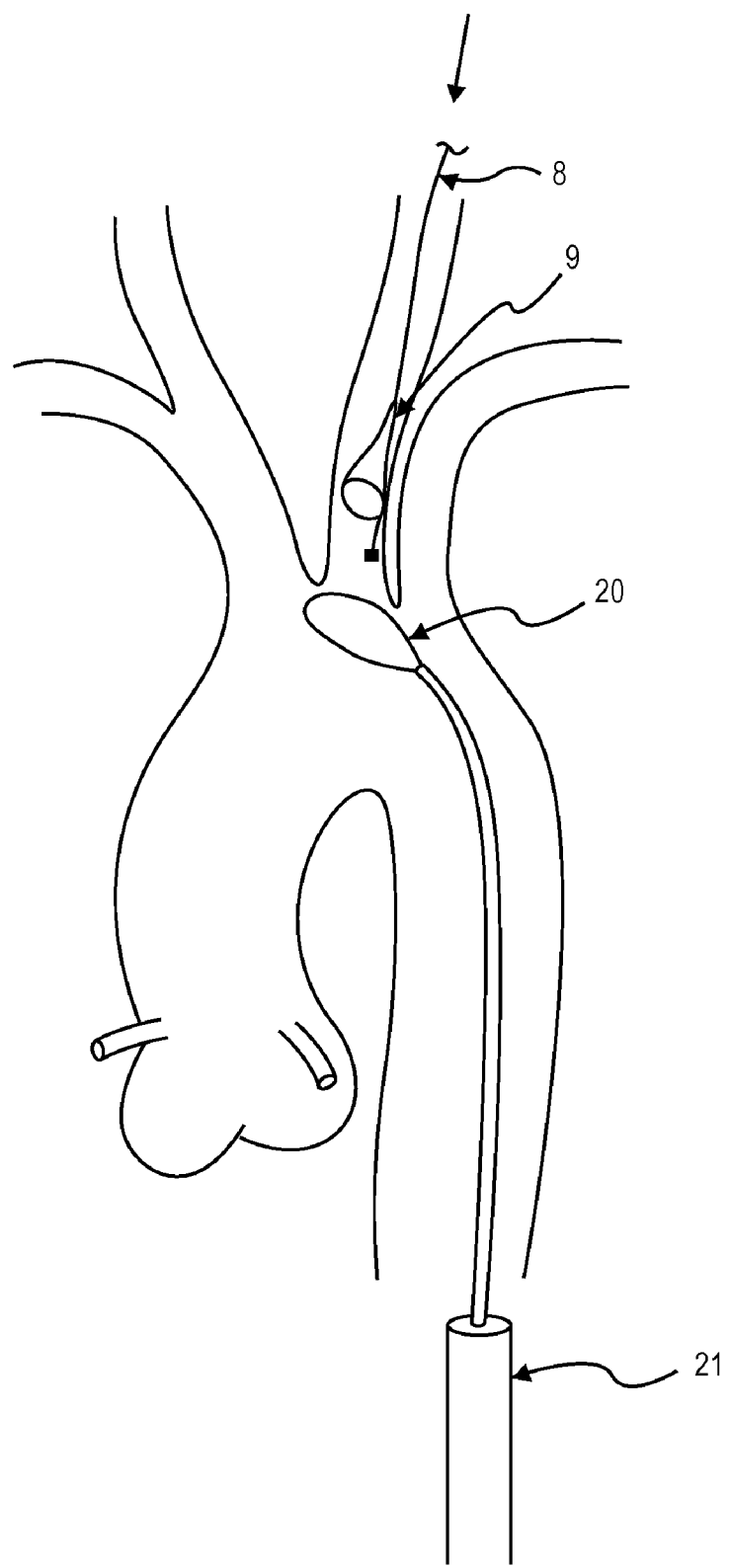
FIG. 13 illustrates a filter 9 delivered over the guidewire 8 from the carotid artery in a retrograde approach just short of the aortic arch. Once the procedure is completed the filter can be snared with a conventional snare 20 to remove it from the body. This will allow for a very small (0.03 inch) entry port in the neck to introduce the device and a larger recovery sheath 21 in the groin where other devices are introduced.
Figure 14:
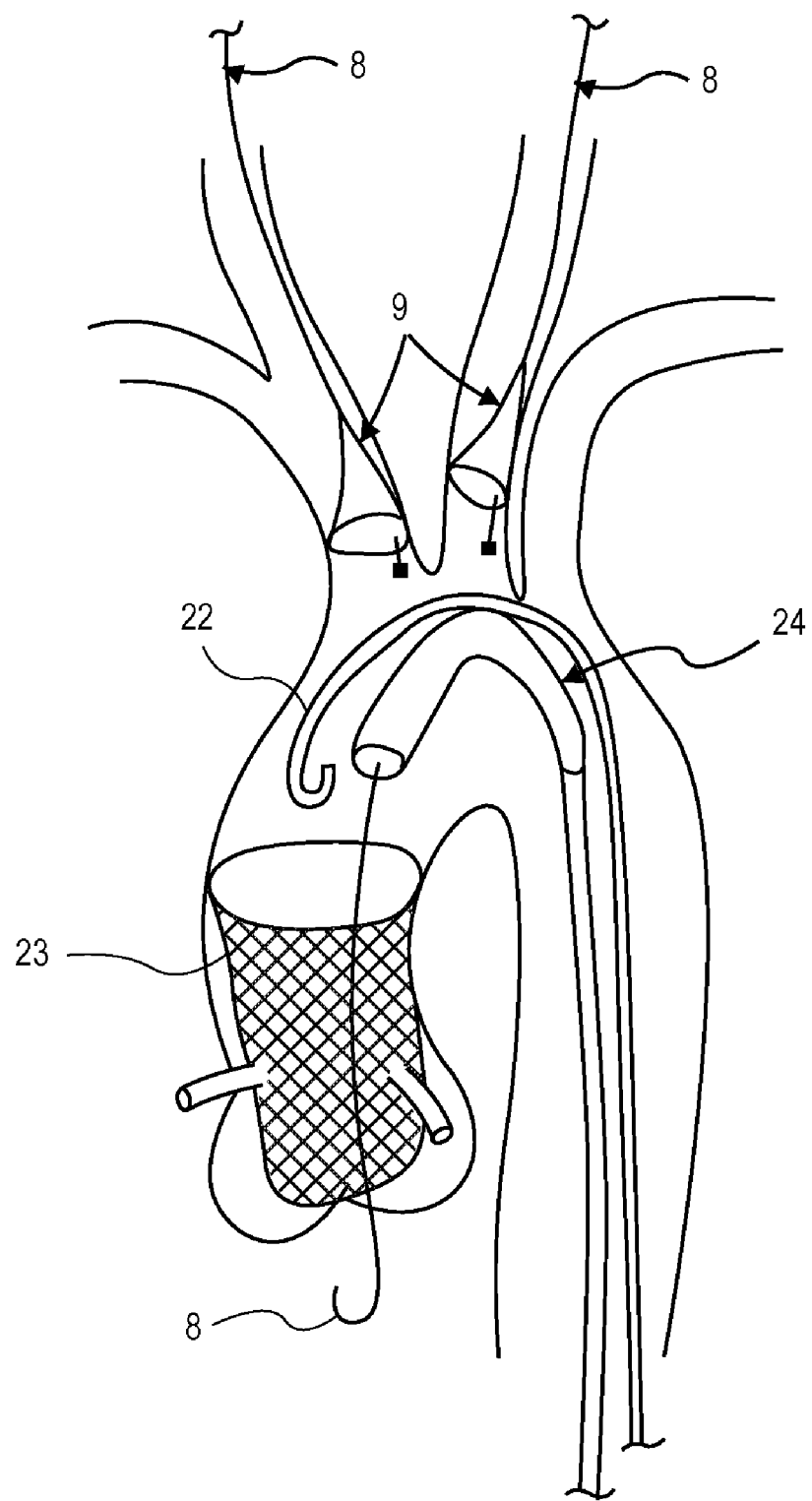
FIG. 14 illustrates a set of filters in the carotid arteries delivered and ready for additional procedures to occur under filtered protection. During a percutaneous heart valve delivery there may be multiple catheters in the aortic arch consuming much of the available area. Shown here is a pigtail catheter 22 and a delivery catheter 24 for a percutaneous heart valve 23 all within the aortic arch. The filters 9 are clear of the aortic space and will not interfere with delivery or withdrawal of these catheters.
Figure 15:
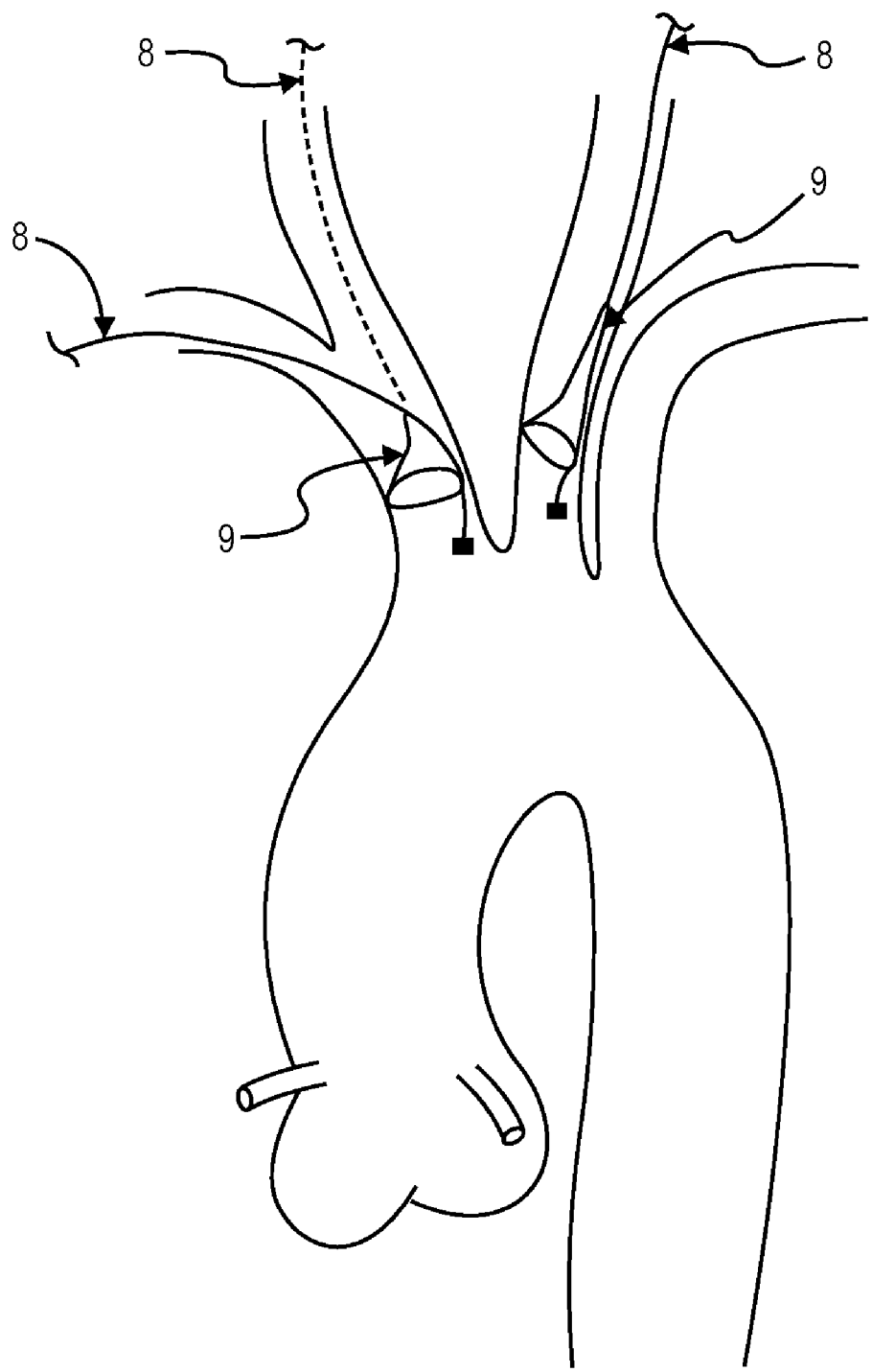
FIG. 15 illustrates another delivery pathway for the placement in the carotid or brachiocephalic trunk. Delivery includes a guidewire 8 introduced via carotid artery or subclavian artery just short of the aortic arch leaving the arch free from interference while delivering other catheters to the heart. These filters 9 can be retrieved either through the groin or recovered back through the entry point in the carotid or subclavian artery.
Figure 16:
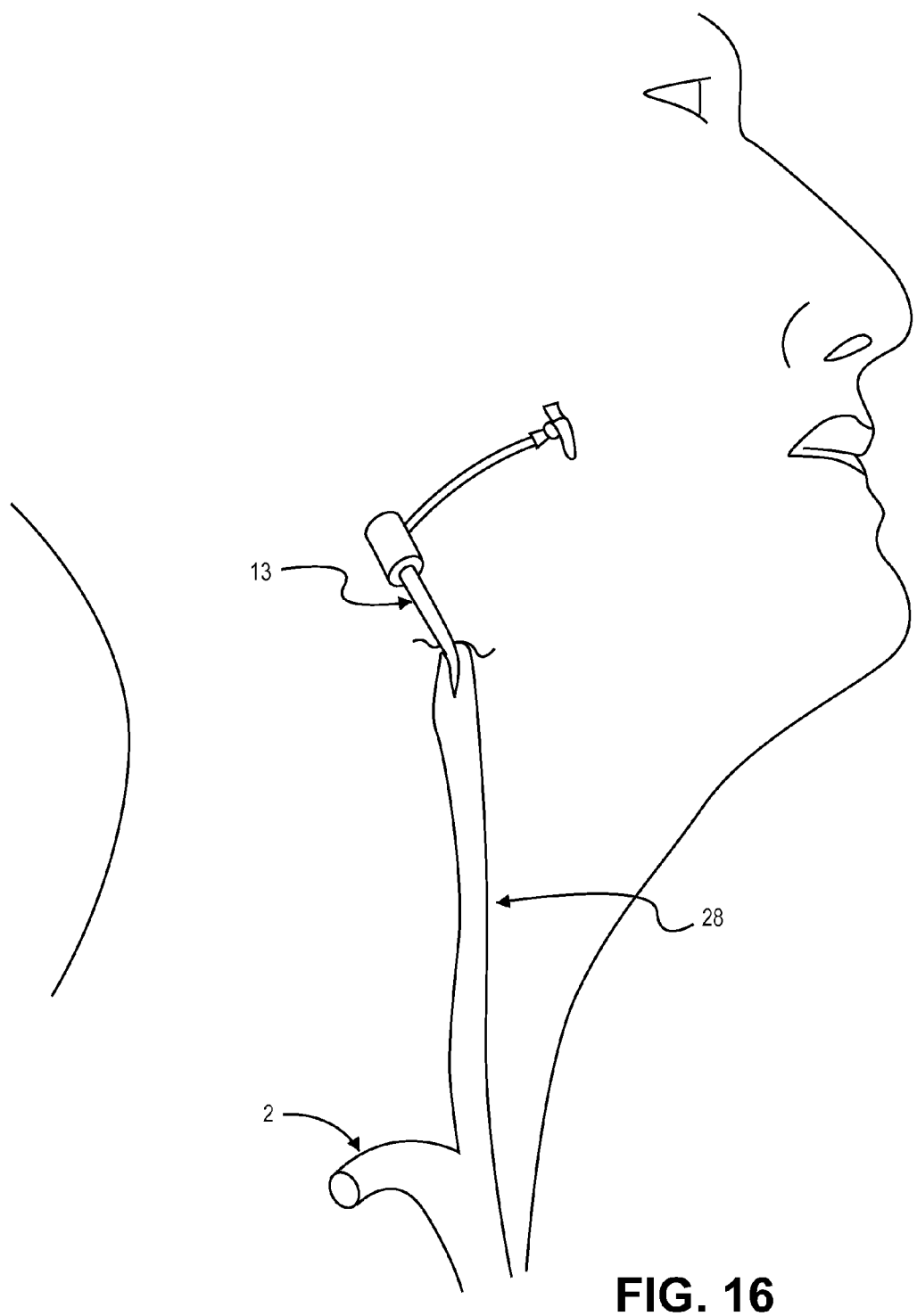
FIG. 16 illustrates a conventional entry to the carotid artery where the sheath is placed in a retrograde manner. A sheath 13 is placed into the carotid artery where access may be gained to the vasculature either antigrade or retrograde depending upon the desired placement of the device.
Figure 17:
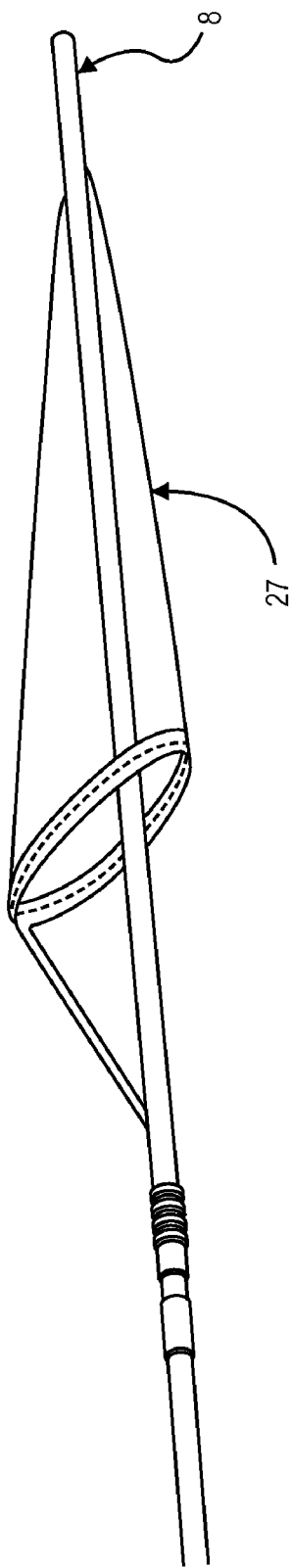
FIG. 17 illustrates an example of a common filter design where the guidewire 8 passes through the central portion of the filter 27. A memory material such as Nitinol is used to expand the filter material to the vessel wall.
Figure 18A:
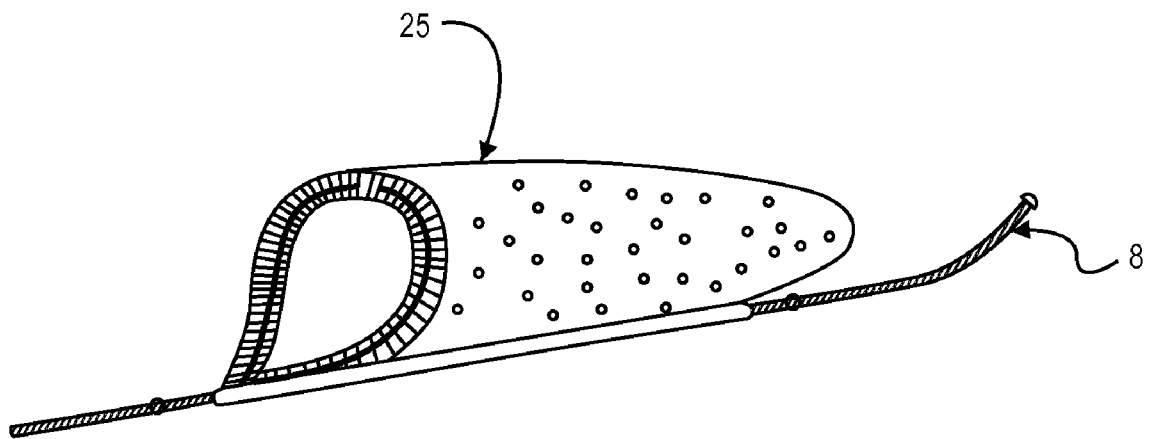
FIG. 18 illustrates other examples of filters where a loop style 25 has the guidewire passing along the side of the device and functions like a wind-sox when deployed in the vessel. The other example is a framed filter where when expanded the filter material is opposed to the vessel wall and the guidewire 8 passes through the central portion of the device.
Figure 18B:
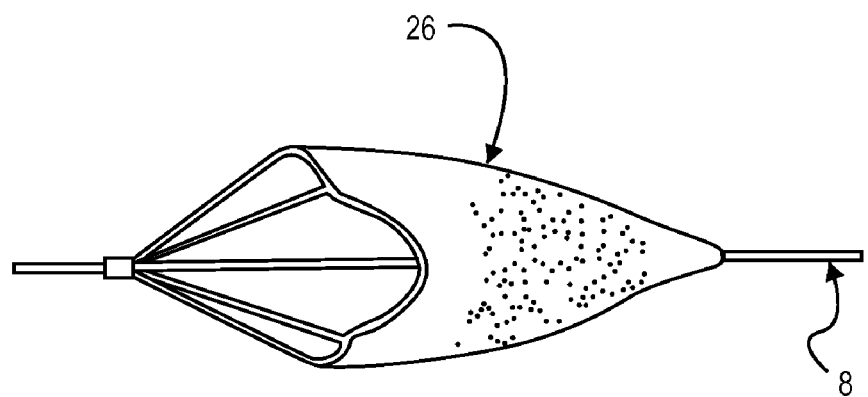

Before standard intervention would occur by a cardiologist a filter would be placed into the carotid arteries to protect the circulation to the brain where emboli could induce a stroke and leave the patient debilitated. Placement of these filters to the patient's carotid circulation would be most convenient if it occurred without obstruction of the aorta where other catheters would be passed and preferably on the patient's right side as it is common practice for the doctor to steer the catheters from this side of the table. Standard practice is to gain access in the right femoral artery where a sheath would be placed to introduce catheters, guidewires and other device delivery means. This would leave the left femoral artery open but often it too is used for other diagnostic catheters and it is less convenient to work across the patient's body. Other access sites would include carotid entry but the neck area is often again inconvenient to operate from and generally too far from the other wires and catheters. The final entry point would be a radial or an arm entry where a sheath would be placed into the brachial or radial artery for access to the subclavian artery and more distally the aorta and the carotid arteries. This approach would allow the doctor to access the patient's right arm placing a sheath into the radial artery and delivering catheters, guidewires and sheaths to the carotid arteries. After a 5 French sheath placement a guide catheter would be placed into the radial artery and advanced to the brachiocephalic trunk where the right carotid artery meets the subclavian. From here a curve in the guide catheter would allow a 180 turn to occur accessing from the brachiocephalic trunk into the aortic arch and back up the left carotid artery which is commonly found one centimeter down the aortic arch. Once the guide catheter is place a filter may be advanced into the left carotid artery and deployed leaving this vessel protected from emboli. The guide catheter could be moved proximally to leave this vasculature and back into the brachiocephalic trunk artery where a coaxial filter could now be placed protecting this carotid artery. The connection between the two filters is a common axial link where the distal or left carotid filter would be attached to a 0.014 inch guidewire as normally constructed and the more proximal filter would utilize a tubular member such as a polymer or Nitinol hypo tube. The distal filter may need to be gently engaged to the vessel wall to allow the connection guidewire to be tensioned removing any slack or loop within the aortic arch. This may be possible with engagement barbs restricting proximal motion of the device in the vessel when deployed. Other means may be a stronger force in the memory metal loop to keep the device opposed to the wall. Now the circulation to the brain is protected and the aortic arch is clear from obstruction the normal procedure can occur. Examples of these procedures include but are not limited to:

Coronary stenting
Aortic valve replacement via catheterization
Aortic or mitral valve replacement via transapical
Aortic balloon valvuloplasty
Mitral valvuloplasty
Mitral valve replacement via catheterization
Diagnostic catheterization
Surgical valve replacement (aortic or mitral)
Surgical valve repair (aortic or mitral)
Annuloplasty ring placement
Atrial fibrillation catheterization
PFO closure (surgical or catheter based)
Left atrial appendage closure (catheter or surgical)

Once the procedure has been completed the filters may be removed immediately or left in place if an antitrombotic coating is added or the patient remains on blood thinning agents to limit clot from forming on the filters. It may be advantageous to leave the filters in for a period of twenty four hours as the patient begins to recover. When removal is necessary the goal is to not dislodge any trapped emboli within the filter. Conventionally this is accomplished by pulling the filter into a larger recovery sheath to first close the open end of the filter and draw the remaining portion safely back into the recovery catheter. With the filters being opposed in direction it may be advantageous to move the distal filter into the proximal filter and recover them both together in a nested orientation.

What is claimed is:

1. A method of filtering a subject's blood to prevent foreign material from traveling into the carotid circulation, comprising:
   providing a filter system comprising a first tubular member to which a first filter is mounted and a second tubular member to which a second filter is mounted, wherein the first and second tubular members are disposed in a coaxial manner and moveable relative to each other to provide for relative motion between the first and second filters;
   introducing the filter system into the subject and advancing the filter system into the subject's right subclavian artery; and
   expanding the first and second filters in a manner such that the second filter is expanded in the subject's brachiocephalic trunk and the first filter is introduced in a collapsed configuration and expanded in the subject's left common carotid artery.

2. The method of claim 1 further comprising the steps of:
   advancing the first filter relative to the second filter and expanding the first filter in the subject's left common carotid artery wherein expanding the first filter in the left common carotid artery occurs prior to the expansion of the second filter in the brachiocephalic trunk.

3. The method of claim 1 wherein expanding the first and second filters comprises positioning the first and second filters in opposite directions relative to one another.

4. The method of claim 1 further comprising the steps of:
   providing a guidewire over which the first and second tubular members are advanced;
   advancing at least the first tubular member over the guidewire to position the first filter in the left common carotid artery; and
   expanding the first filter in the left common carotid artery.

5. The method of claim 1 wherein the first tubular member has a distal end and further comprising the step of actively and controllably shaping the distal end of the first tubular member to access the left common carotid artery.

6. The method of claim 5 further comprising the steps of:
   providing a handle mechanism external to the subject having an actuation member for controllably shaping the distal end of the first tubular member; and
   actuating the actuation member to controllably shape the distal end of the first tubular member.

7. The method of claim 6 wherein the step of actuating the actuation member comprises applying tension to the distal end of the first tubular member through a pull wire.

* * * * *